United States Patent [19]

Sherman

[11] 4,382,927

[45] May 10, 1983

[54] PHOSMET-DIFLUBENZURON INSECTICIDAL COMPOSITION

[75] Inventor: Esmeralda R. Sherman, Pacifica, Calif.

[73] Assignee: Stauffer Chemical Company, Westport, Conn.

[21] Appl. No.: 282,469

[22] Filed: Jul. 13, 1981

[51] Int. Cl.³ .................. A01N 57/10; A01N 47/28; A01N 57/16
[52] U.S. Cl. .................................... 424/200; 424/322
[58] Field of Search ............................... 424/200, 322

[56] References Cited

U.S. PATENT DOCUMENTS

| | | | |
|---|---|---|---|
| 2,767,194 | 10/1956 | Fancher | 424/200 |
| 3,743,728 | 7/1973 | Fancher | 424/200 |
| 3,748,356 | 7/1973 | Wellinga et al. | 424/322 |
| 4,263,287 | 4/1981 | Dennis | 424/200 |

OTHER PUBLICATIONS

*Chemical Abstracts,* vol. 86, 1977, p. 113.

*Primary Examiner*—Nicky Chan
*Assistant Examiner*—F. T. Moezie
*Attorney, Agent, or Firm*—Joel G. Ackerman

[57] ABSTRACT

Mixtures of the commercial insecticides phosmet and diflubenzuron, in a weight ratio of about 3:1–1:3, have been found to possess a synergistic effect.

8 Claims, No Drawings

PHOSMET-DIFLUBENZURON INSECTICIDAL COMPOSITION

BACKGROUND AND PRIOR ART

This invention relates to a new and unexpectedly synergistic insecticidal composition containing the commercial insecticides phosmet and diflubenzuron, and particularly containing these compounds in a weight ratio of from about 1:3 to about 3:1.

Phosmet is the generic name of the commercial insecticide N-(mercaptomethyl)phthalimide S-(O,O-dimethylphosphorodithioate), which has the formula

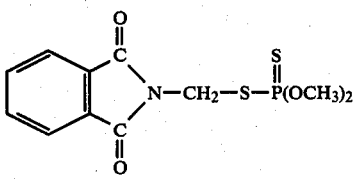

and is disclosed for instance, in U.S. Pat. No. 2,767,194. This compound is sold under several trademarks including the registered trademark Imidan ® and Prolate ®.

Diflubenzuron is the generic name for the commercial insecticide N-[[(4-chlorophenyl)amino]carbonyl]-2,6-difluorobenzamide, which has the formula

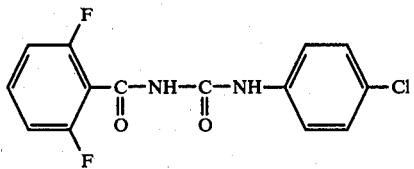

and is sold under the name Dimilin ®.

Both of these insecticides have been in commercial use for some years and have been registered for use against various insects. Diflubenzuron, in particular, is known to control insects by causing inhibition of molting.

As substantiated by test results which follow, it has been determined that a combination of these two insecticides, in a weight ratio of from about 3:1 to about 1:3, and particularly from about 3:1 to about 1:1, of phosmet:diflubenzuron, possesses unexpected activity in controlling insects, particularly the larvae of the cabbage looper, (*Trichoplusia ni*), beet armyworm, (*Spodoptera exigua*), and tobacco budworm (*Heliothis virescens*), and other insects of this same genera.

EXPERIMENTAL PROCEDURE AND RESULTS

Tests were conducted using combinations of phosmet and diflubenzuron at weight ratios ranging from 3:1 to 1:3, respectively, as well as the individual insecticides, against three insects: the cabbage looper [*Trichoplusia ni* (Hubner)], the tobacco budworm [*Heliothis virescens* (Fabricius)], and the beet armyworm (*Spodoptera exigua*). Test procedures were utilized as follows:

Cabbage Looper—[*Trichoplusia ni* (Hubner)]: Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with five second-instar cabbage looper larvae. Mortality of the larvae was recorded 5 days later.

Tobacco Budworm—[*Heliothis virescens* (Fabricius)]: Test compounds were diluted in a 50-50 acetone-water solution. Cotyledons of Cotton (*Gossypium hirsutum*) were immersed in the test solutions for 2-3 seconds and placed on a wire screen to dry. The dried leaves were placed in petri dishes containing moistened filter paper and infested with five second-instar tobacco budworm larvae. Mortality of the larvae was recorded 5 days later.

Beet Armyworm (*Spodoptera exigua*): Test compounds were diluted in a 50-50 acetone-water solution. Sugarbeet cotyledons (*Beta vulgaris*) were immersed in the test solutions for 2-3 seconds and placed on a wire screen to dry. The dried leaves were placed in petri dishes containing a moistened filter paper and infested with five second-instar beet armyworm larvae. Mortality of the larvae was recorded five days later.

Test concentrations ranged from 0.1% to that at which approximately 50% mortality occurred, and calculated according to dosage-mortality curves. LD-50 values are expressed below in Table I under the headings "CL", "TBW", and "BAW" respectively, in terms of percent of the test compound in the solution.

The results of these tests are shown in the following Table I.

TABLE I

| Insecticide | Average of Four Replications $LD_{50}$ | | |
|---|---|---|---|
| | CL | TBW | BAW |
| Phosmet | 0.01 | 0.03 | 0.04 |
| Diflubenzuron | 0.04 | 0.007 | 0.001 |
| Phosmet:diflubenzuron by Weight: 3:1 | 0.009 | 0.01 | 0.001 |
| 1:1 | 0.004 | 0.006 | 0.0005 |
| 1:3 | 0.004 | 0.009 | 0.0008 |

From the data in Table I relating to the performance of the individual insects, the expected additive effect of a mixture of the two was determined; it was then compared with the observed insecticidal effect of the mixture to determine whether or not the latter was substantially greater than the former. If the insecticidal effect actually observed of the mixture is substantially greater than the expected effect, the performance is considered to exhibit a synergistic effect or, in other words, unobvious results.

The determination of this question was performed by calculating the cotoxicity coefficients of mixtures of phosmet and diflubenzuron, using the method of Yun-Pei Sun and E. R. Johnson, *Journal of Economic Entomology*, 1960, Volume 53, No. 5, pages 887–892. See also U.S. Pat. No. 4,182,772.

The cotoxicity coefficient is the ratio of the actual toxicity index (T.I.) of the mixture to its theoretical toxicity index:

$$\text{Cotoxicity coefficient} = \frac{\text{Actual } T.I. \text{ mixt.}}{\text{Theoretical } T.I. \text{ mixt.}} \times 100$$

The actual toxicity index of the mixture is determined by dividing the $LD_{50}$ of the more active individual component, (referred to herein as the "standard") by the $LD_{50}$ of the mixture, and is determined separately for each weight ratio of components, and for each insect:

$$\text{Actual } T.I. \text{ mixt.} = \frac{LD_{50} \text{ standard}}{LD_{50} \text{ mixt.}} \times 100$$

The more active component for the cabbage looper was phosmet; for the tobacco budworm and beet armyworm, it was diflubenzuron.

The theoretical toxicity index for the mixture is determined as follows:

Theoretical T.I. mixt.=Actual T.I. component
A×% of A in mixture+Actual T.I. component
B×% of B in mixture.

The actual toxicity index of each component ("A" and "B") is determined by dividing the activity of the "standard" component by that of the component in question:

$$\text{Actual } TI \text{ of each component} = \frac{LD_{50} \text{ standard}}{LD_{50} \text{ component}} \times 100$$

When the component in question is the "standard", this value becomes 100.

If the cotoxicity coefficient of a mixture, calculated as above, exceeds 100, synergism is considered to have been exhibited.

The cotoxicity coefficients of the mixtures in Table I are contained in the following Table II.

TABLE II

| Insect | Weight Ratio* | Cotoxicity Coefficient |
| --- | --- | --- |
| Cl | 3:1 | 136.8 |
|  | 1:1 | 400.0 |
|  | 1:3 | 571.4 |
| TBW | 3:1 | 164.7 |
|  | 1:1 | 189.2 |
|  | 1:3 | 96.2 |
| BAW | 3:1 | 372.1 |
|  | 1:1 | 390.2 |
|  | 1:3 | 165.3 |

*Phosmet:diflubenzuron

The compositions or formulations including the two insecticides described herein may take a number of solid or liquid forms. Even a mixture of the pure compounds could be used as an insecticide. However, in general, such insecticides are first formulated with one or more inert (i.e., plant compatible or herbicidally inert) carriers or diluents suitable for insecticidal use, before being applied.

Solid forms of compositions containing the insecticides could be, for instance, dusts, granules, tablets, powders and the like. Liquid forms could be, for instance, emulsions, solutions, suspensions, emulsifiable concentrates, flowables and pastes. Such solid and liquid compositions, in addition to the active compounds, would contain various carriers or diluents, surface-active agents, solvents, adhesives, thickeners, binders, anti-foaming agents and other substances. Solid carriers or diluents included in certain compositions or formulations may include, for instance, ground natural minerals, such as kaolins, alumina, calcium carbonate, silica, kieselguhr, clay, etc.; ground synthetic minerals such as silicates and aluminisilicates, and ground vegetable products such as bark, cornmeal, sawdust, cellulose powder and the like.

It is possible to use highly concentrated liquid compositions containing up to about 95% by weight of the active ingredients, or even the pure compounds alone, when applying them in the form of a finely divided liquid by use of various atomizing equipment such as airplane crop sprayers. For other purposes, however, the various types of compositions which can be utilized for these compounds will contain varying amounts of the compound according to the type of composition and intended use.

In general, compositions may contain from 5 to 95% by weight of the active compounds, more preferably 10 to 85%. Some typical compositions will contain active compounds as follows; wettable powders: 25–80% by weight; oil suspensions, emulsions, solutions and emulsifiable concentrates: 20–80% by weight, aqueous suspensions; 20–50% by weight; dusts and powders; 50 to 20% by weight; granules and pellets: 5 to 20% by weight.

In addition to the active compounds and the various formulating agents, compositions containing these compounds may also contain one or more other active pesticidal agents such as herbicides, fungicides, insecticides, acaricides, nematocides, bactericides and plant growth regulators. Such compositions may also contain fertilizers, thus making it possible to provide multi-purpose compositions containing mixtures of phosmet and diflubenzuron, as well as optionally other pesticides and also fertilizers, all intended and formulated for use at the same locus.

To control insect pests using the inventive mixture a composition containing an insecticidally effective amount of such mixture is applied to the insect, to a locus at which insect control is desired, or to food sources (including seeds) on which the insects feed. Thus control may be achieved by direct application of the phosmet/diflubenzuron mixture to the insect and/or indirectly by application of the mixture to the locus to be protected such as crops or crop land, or to breeding or swarming areas. The rate of application of the mixture and the concentration applied will vary according to whether it is being directly or indirectly applied to control the insect. In the cases of application to a crop area, depending on the nature of the insect to be controlled and the plant environment the application rate will generally vary from 0.01 to about 2, preferably from about 0.5 to about 2 lbs./acre, of the mixture.

Compositions containing the phosmet/diflubenzuron mixture may be applied in any convenient manner. When used in connection with crop or plant protection, application of the mixture may be performed in a preventive (i.e., before infestation) or eradicative (i.e., after infestation) manner. Thus, various compositions containing the mixture can be applied by the use of power dusters, boom and hand sprayers, spray dusters or airplane crop dusters or sprayers. Compositions containing the mixture may also be applied by addition to irrigation waters supplied to the field to be treated.

Examples of compositions employing this phosmet/diflubenzuron mixture are:

| (A) | Granular Formulation | | |
| --- | --- | --- | --- |
|  | Phosmet/Diflubenzuron (weight ratio 3:1) |  | 5 wt. % |
|  | Attapulgite Clay |  | 95 wt. % |
|  |  | Total | 100 wt. % |
| (B) | Emulsifiable Concentrate | | |
|  | Phosmet/Diflubenzuron (weight ratio 1:3) |  | 85 wt. % |
|  | Aromatic naphtha solvent |  | 10 wt. % |
|  | Emulsifier |  | 5 wt. % |
|  |  | Total | 100 wt. % |

What is claimed is:

1. An insecticidal composition comprising insecticidal amounts of phosmet and diflubenzuron in a weight ratio of phosmet:diflubenzuron of from about 3:1 to about 1:3.

2. A composition according to claim 1 in which the weight ratio is about 1:1.

3. A method for controlling undesirable insects by applying to the insect, the locus thereof, or a locus at which control is desired, an insecticidal composition comprising insecticidally effective amounts of phosmet and diflubenzuron in a weight ratio from about 3:1 to about 1:3.

4. A method according to claim 3 in which the weight ratio is about 1:1.

5. A method according to claim 3 in which the insect to be controlled is *Trichoplusia ni*.

6. A method according to claim 3 in which the insect to be controlled is of the genus Heliothis.

7. A method according to claim 6 in which the insect is *Heliothis virescens*.

8. A method according to claim 3 in which the insect to be controlled is *Spodoptera exigua*.

* * * * *